United States Patent [19]
Scarborough et al.

[11] Patent Number: 5,928,238
[45] Date of Patent: *Jul. 27, 1999

[54] BONE DOWEL CUTTER

[75] Inventors: Nelson Scarborough, Wayside; John W. Morris, Beachwood, both of N.J.

[73] Assignee: Osteotech, Inc., Eatontown, N.J.

[ * ] Notice: This patent is subject to a terminal disclaimer.

[21] Appl. No.: 08/773,191

[22] Filed: Dec. 27, 1996

Related U.S. Application Data

[62] Division of application No. 08/404,255, Mar. 15, 1995, Pat. No. 5,632,747.

[51] Int. Cl.$^6$ ................................................. A61B 17/16
[52] U.S. Cl. .............................. 606/79; 606/96; 408/201
[58] Field of Search ................................ 606/79, 80, 96; 408/201, 204, 58, 72 R, 72 B, 115 R, 115 B, 226, 227, 228, 229

[56] References Cited

U.S. PATENT DOCUMENTS

| | | |
|---|---|---|
| 4,273,117 | 6/1981 | Neuhauser . |
| 4,416,278 | 11/1983 | Miller . |
| 4,553,575 | 11/1985 | Brown . |
| 4,559,936 | 12/1985 | Hill . |
| 4,573,448 | 3/1986 | Kambin . |
| 4,649,918 | 3/1987 | Pegg et al. . |
| 4,782,833 | 11/1988 | Einhorn et al. . |
| 4,798,213 | 1/1989 | Doppelt . |
| 4,997,434 | 3/1991 | Seedhom et al. . |
| 5,049,150 | 9/1991 | Cozad . |
| 5,062,845 | 11/1991 | Kuslich et al. . |
| 5,192,321 | 3/1993 | Strokon . |
| 5,197,967 | 3/1993 | Wilson ........................................ 606/79 |
| 5,312,408 | 5/1994 | Brown . |
| 5,380,333 | 1/1995 | Meloul et al. ............................. 606/80 |
| 5,484,437 | 1/1996 | Michelson . |

*Primary Examiner*—Michael Buiz
*Assistant Examiner*—Daphna Shai
*Attorney, Agent, or Firm*—Dilworth & Barrese

[57] ABSTRACT

A device is provided for cutting dowels from a bone mass which is easily disassembled for cleaning and sterilization. The dowel cutter includes an axial mounting member having a proximal end portion configured for engagement with a drill chuck and a distal end portion configured to receive a cylindrical cutting blade, an elongated supporting shaft having a distal end portion configured to support a drill guide, and a securement mechanism formed integral with the mounting member for releasably maintaining the relative orientation of the supporting shaft and the axial mounting member during utilization.

14 Claims, 13 Drawing Sheets

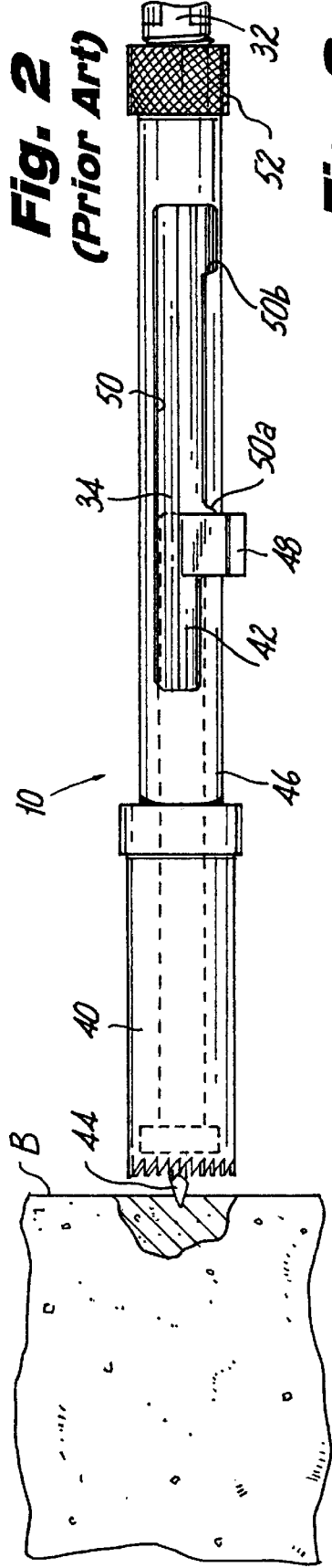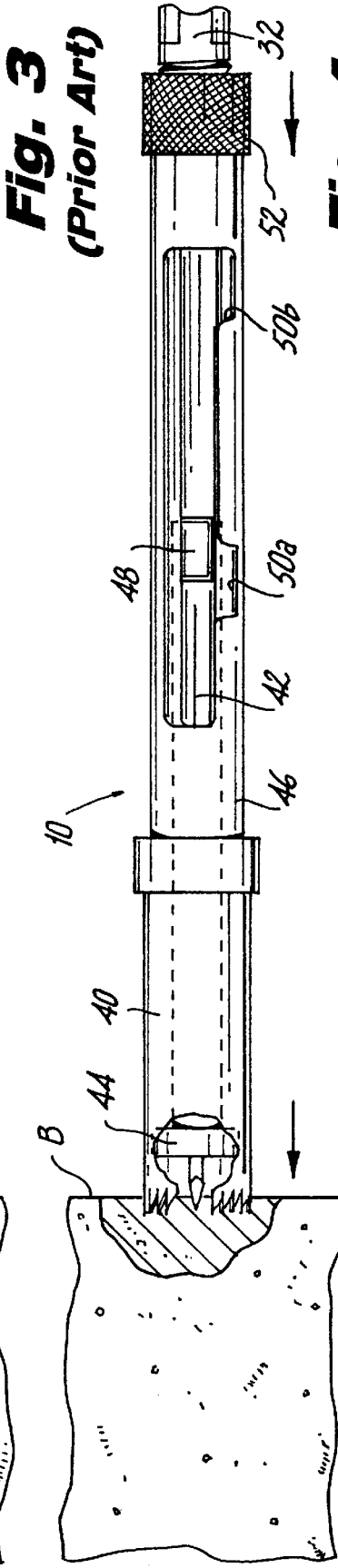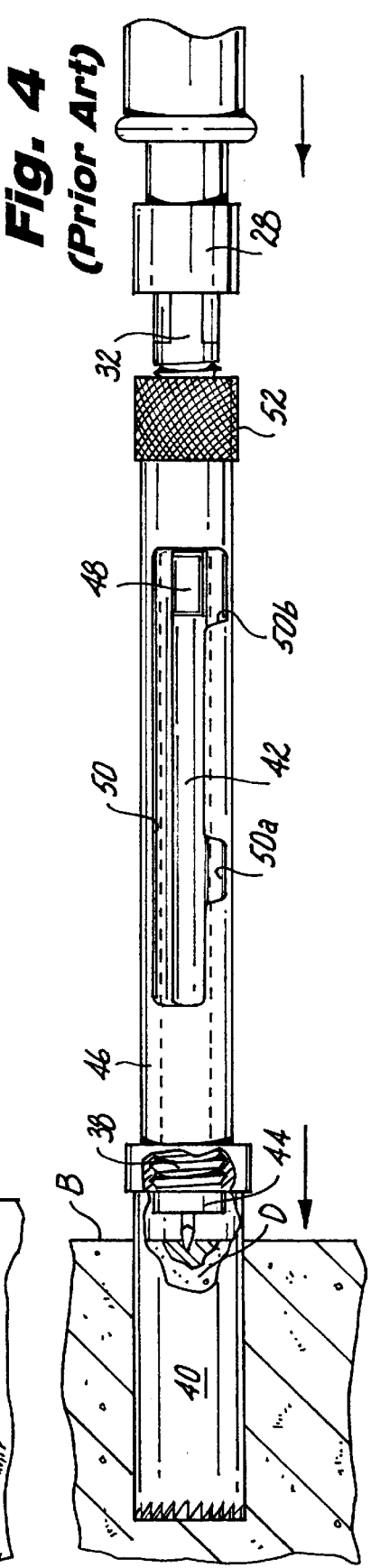

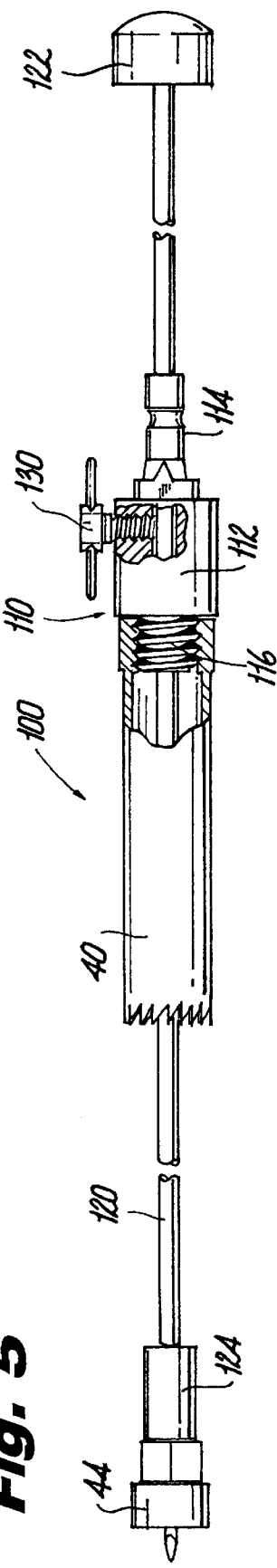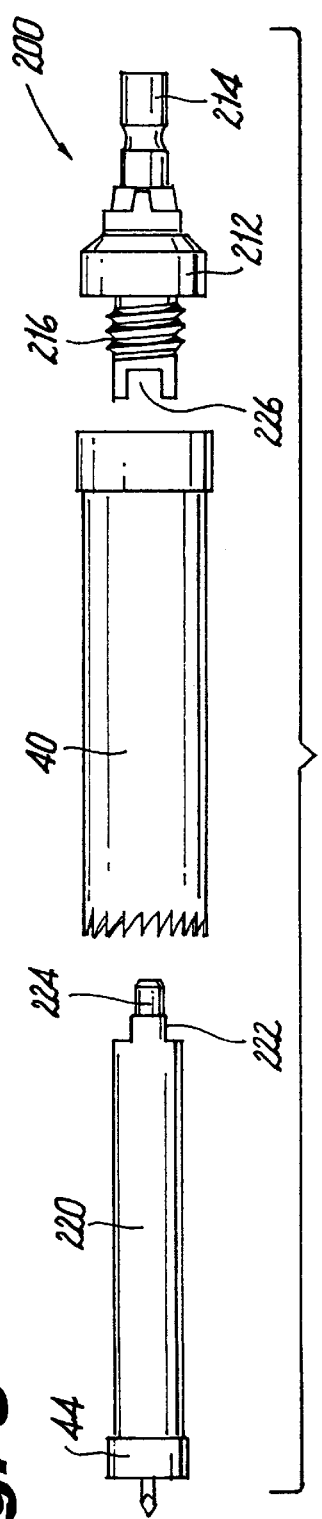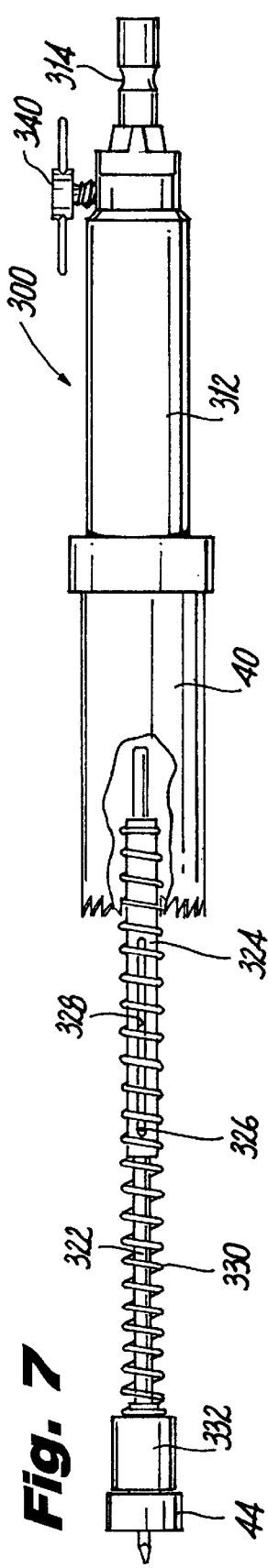

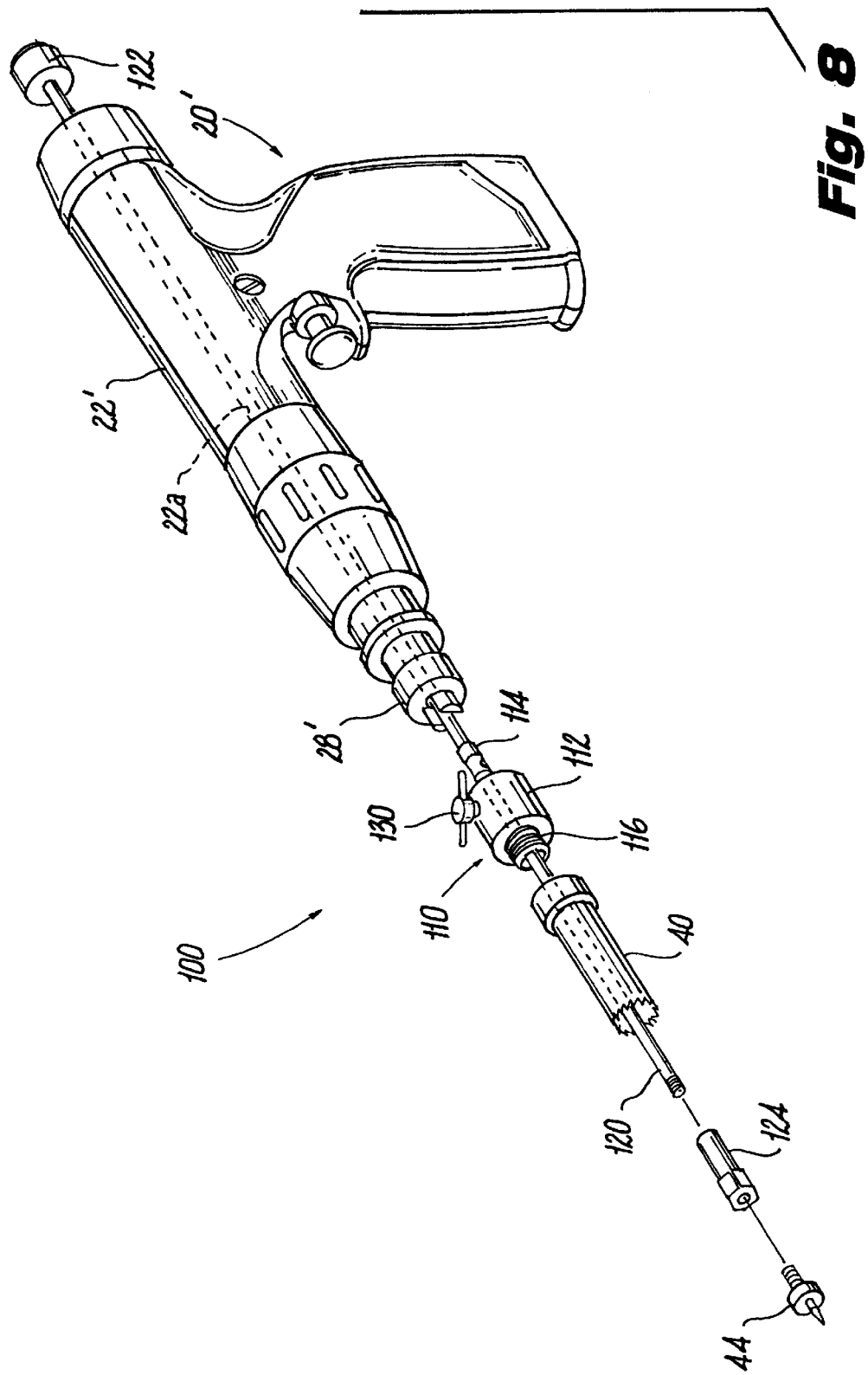

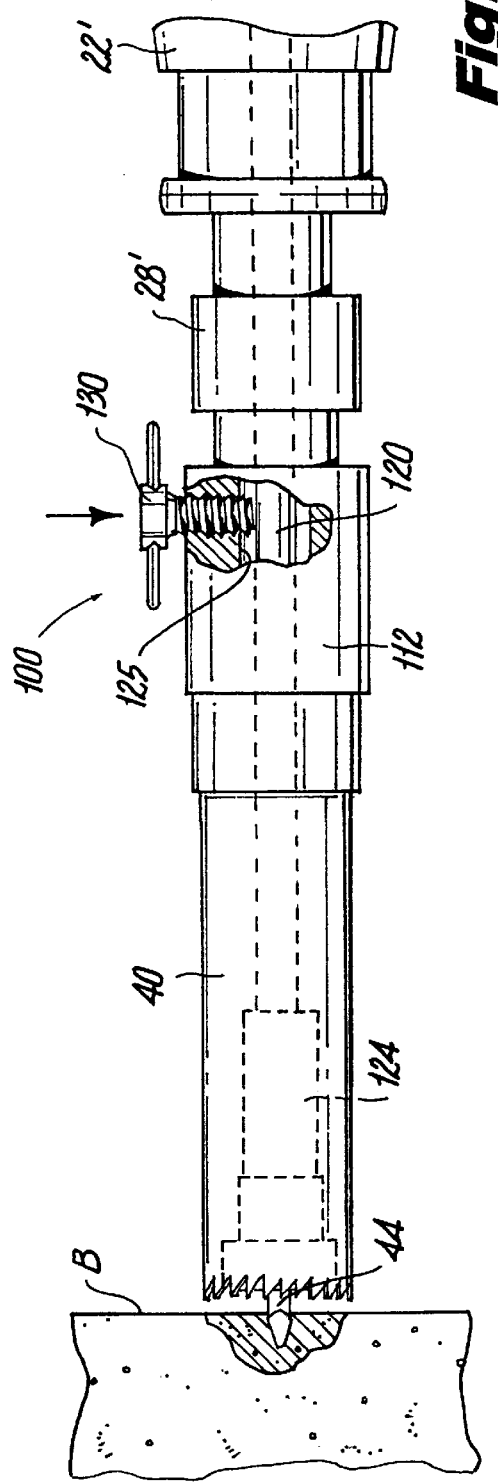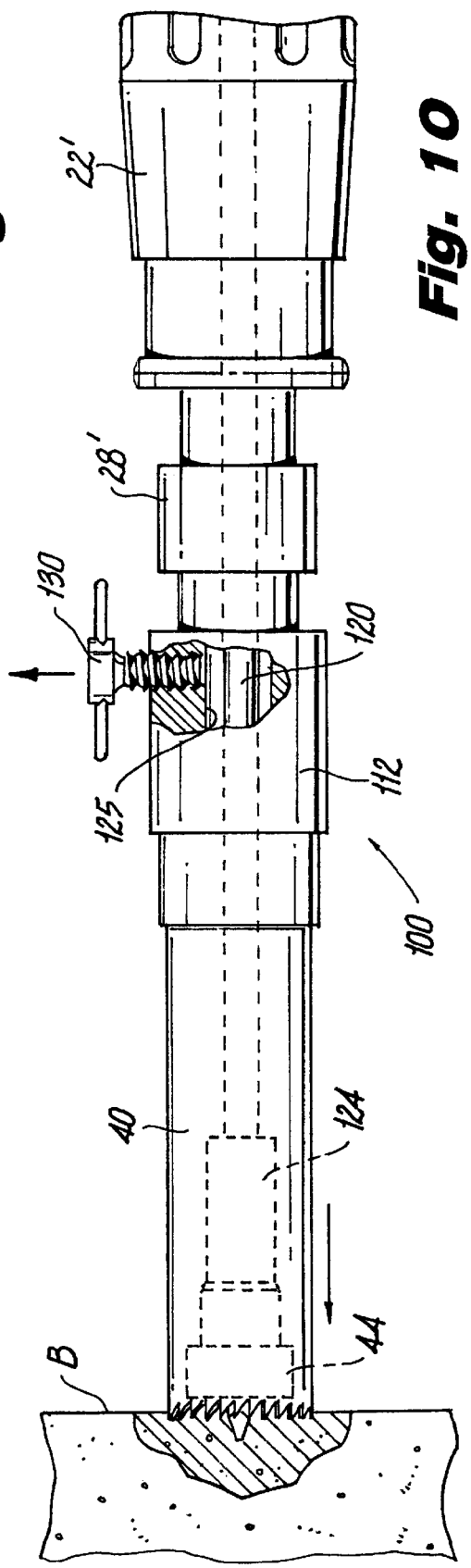

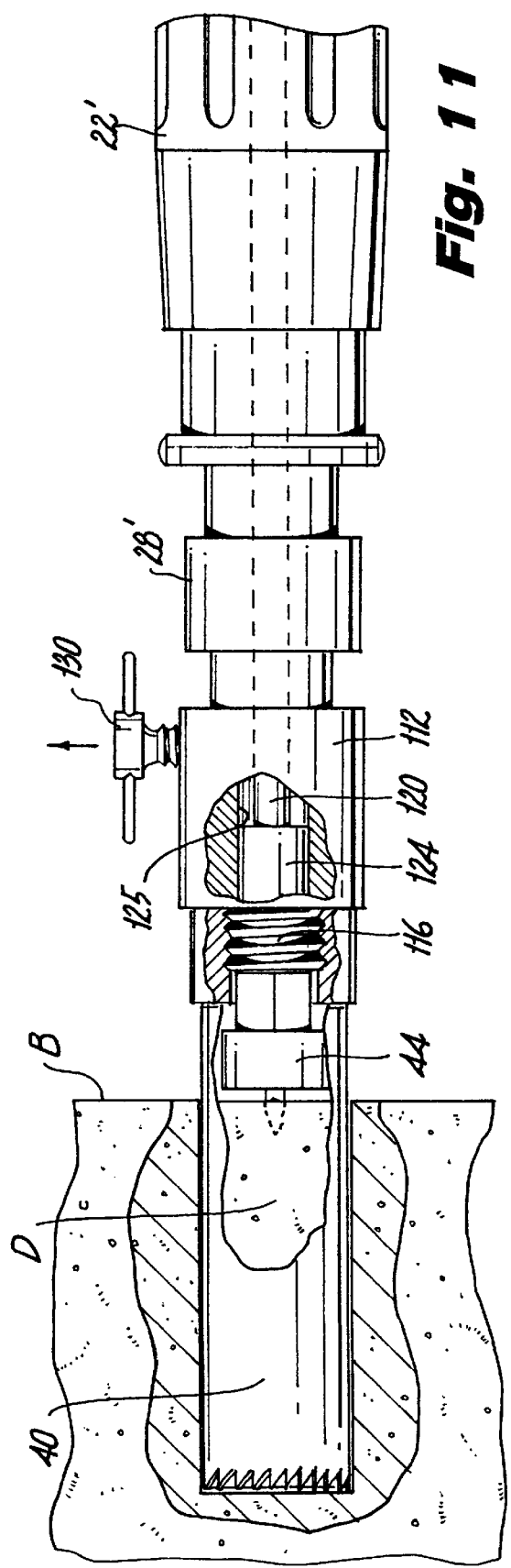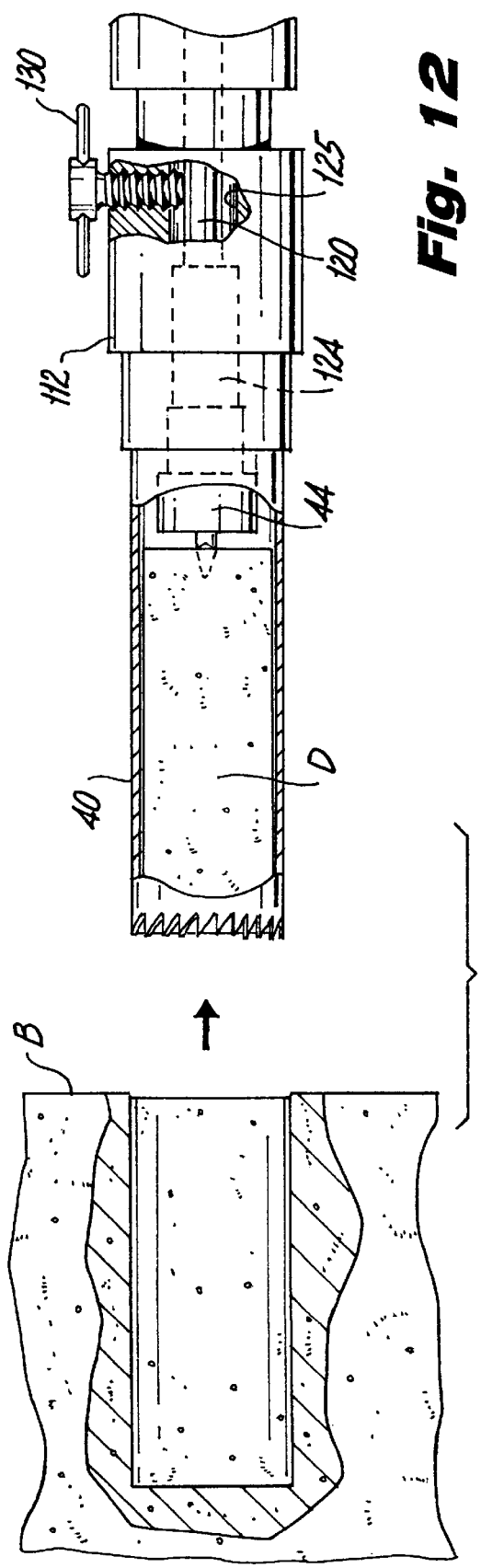

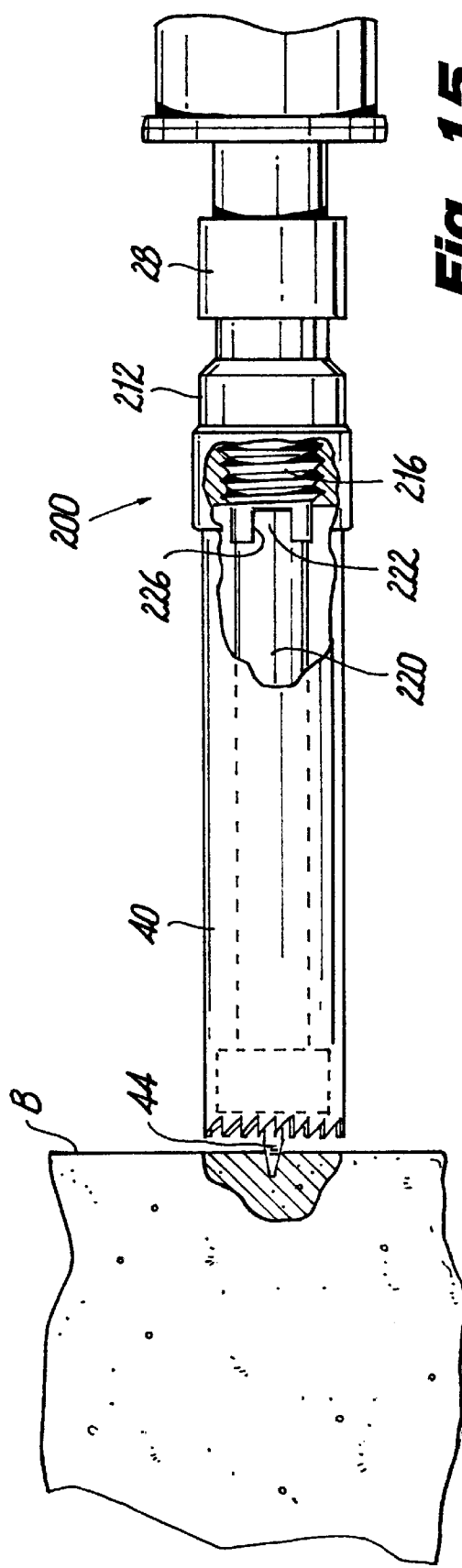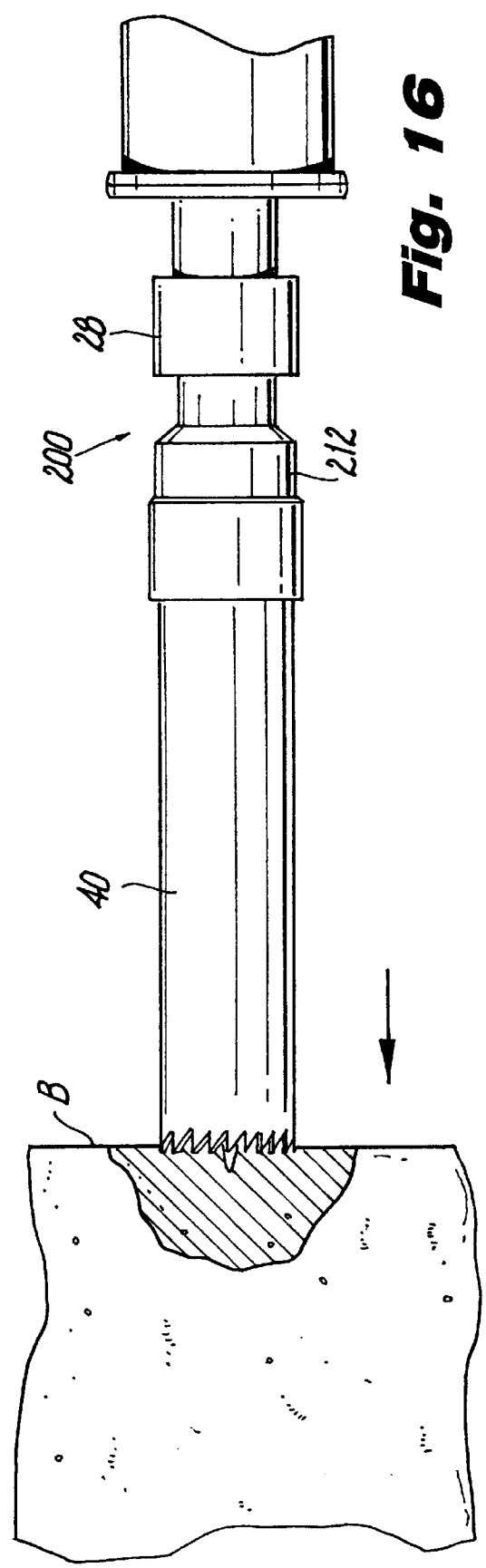

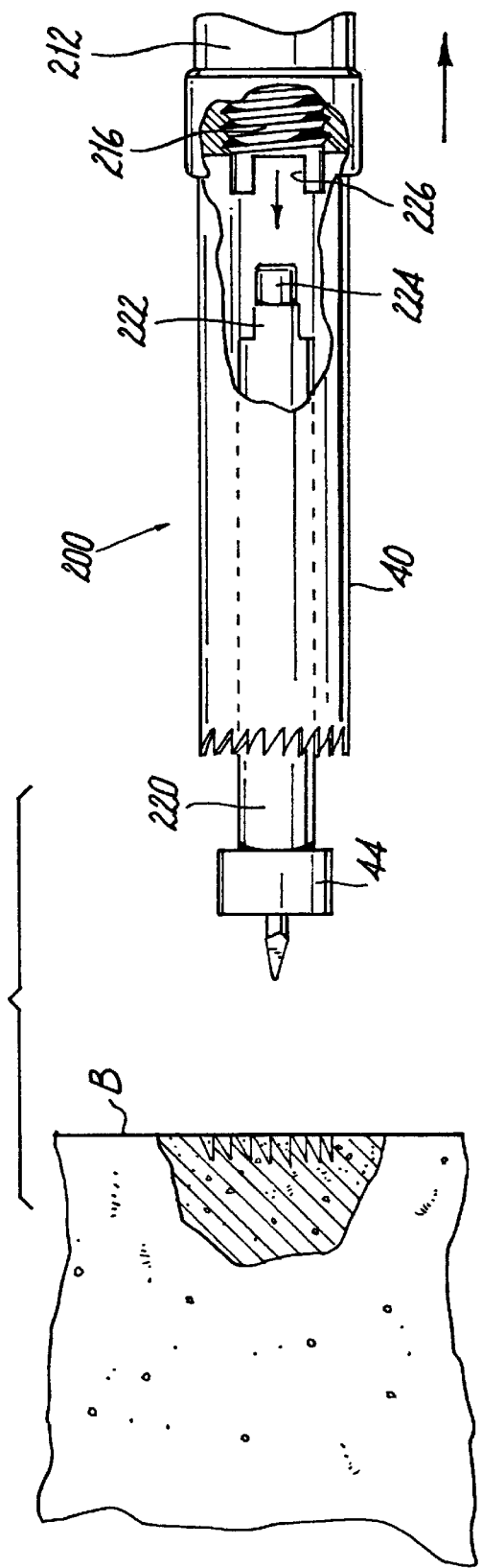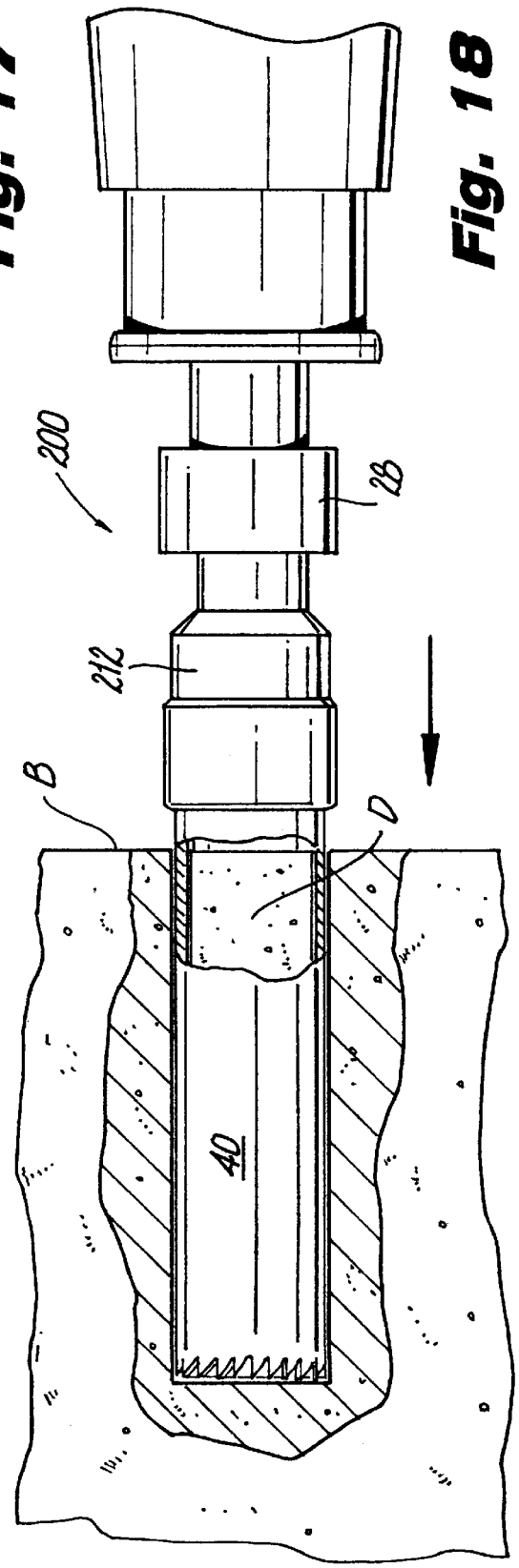

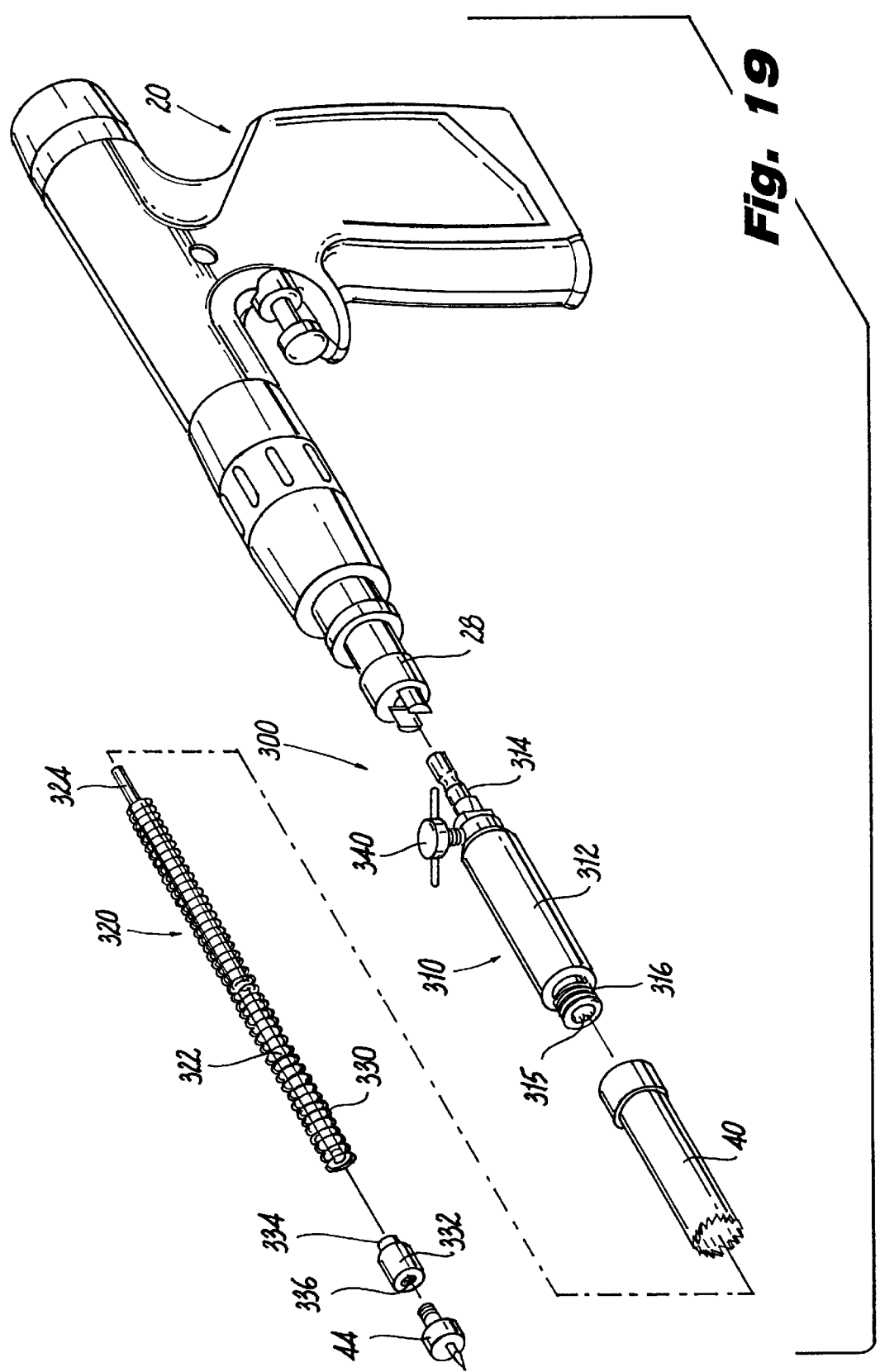

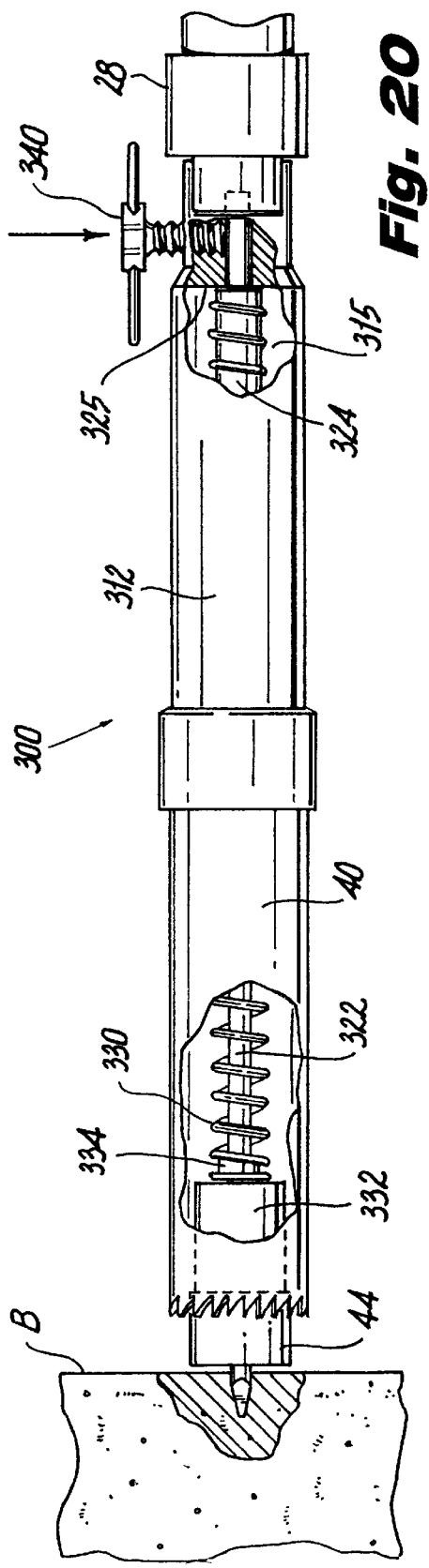
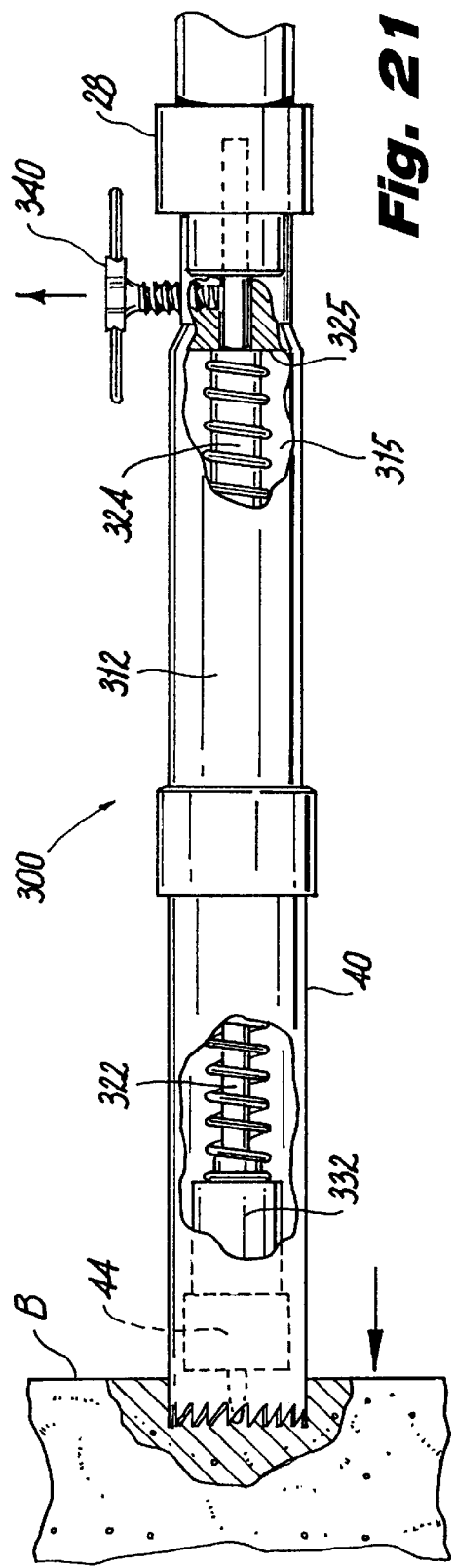

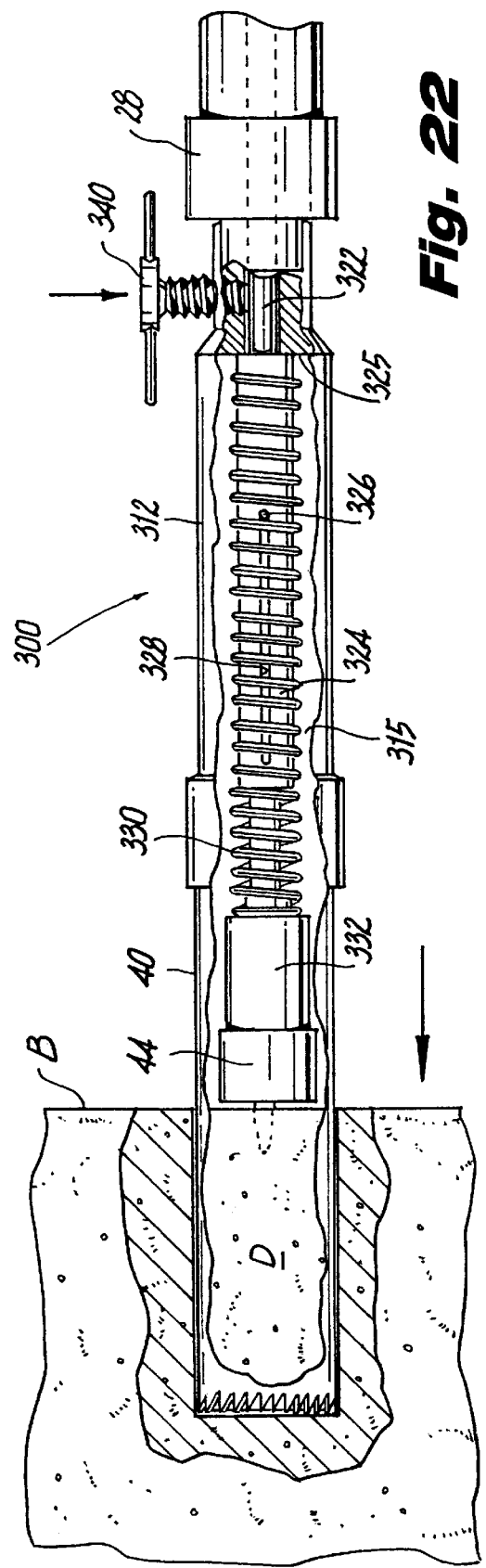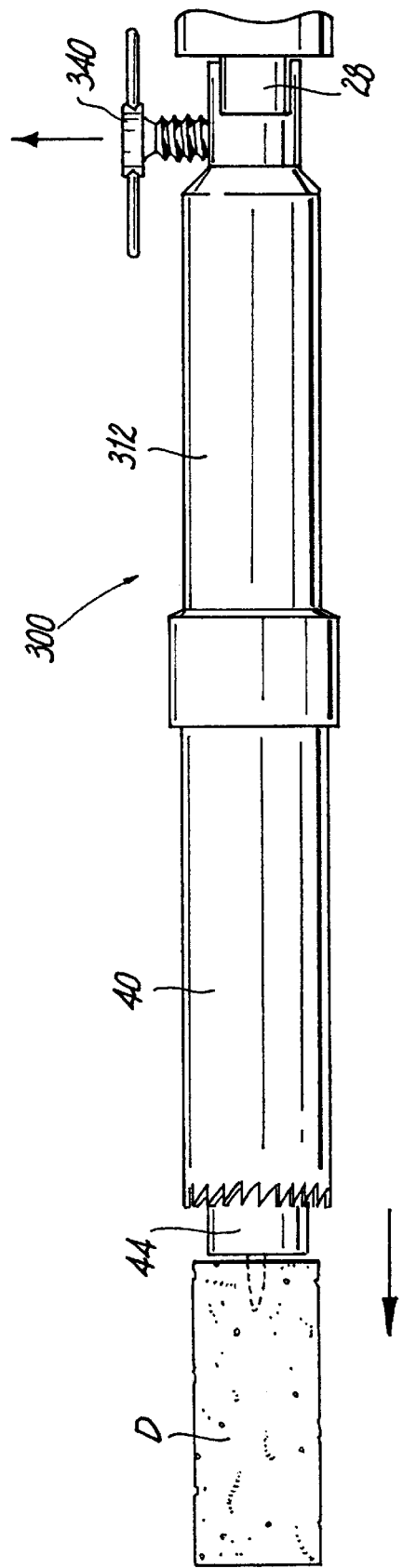

BONE DOWEL CUTTER

This is a divisional of application Ser. No. 08/404,255 filed Mar. 15, 1995 now U.S. Pat. No. 5,632,757.

BACKGROUND OF THE INVENTION

1. Field of the Invention

This invention relates to a device for cutting bone, and more particularly, to an apparatus for cutting dowels from a bone mass.

2. Description of the Related Art

Many osteopathic surgical procedures employ plugs or dowels cut from bone as protheses. Devices for cutting and forming plugs or dowels from bone are known in the art and include both hand-held and platform-mounted configurations. An example of a platform-mounted device is disclosed in U.S. Pat. No. 4,416,278 to Miller which includes a die carried on a plunger that is housed in a sleeve. A pivoting handle which takes the form of a lever is connected to the plunger to effect the movement thereof relative to the sleeve.

Another apparatus for forming bone plugs which has a platform-mounted configuration is disclosed in U.S. Pat. No. 4,559,936 to Hill. This device has a cup-like fixture for supporting the bone from which the plug is cut, and includes a cylindrical cutting tool which rotates axially and translates longitudinally with respect to the bone supporting fixture during a plug forming procedure.

An example of a hand-held apparatus for removing a core from a bone mass is disclosed in U.S. Pat. No. 4,649,918 to Pegget et al. and includes a cylindrical member having a honed cutting edge which is axially rotated to cut the bone core. A similar device is disclosed in U.S. Pat. No. 4,798,213 to Doppelt which is configured to obtain a bone biopsy specimen. The device includes an introducer, a trocar, a manually operated cylindrical cutting drill, and a plunger for removing the bone specimen from the drill.

Another prior art device utilized to cut dowels from bone is manufactured by Cloward™ and is configured to be mounted to a conventional hand-held surgical drill. The Cloward™ device is illustrated in FIGS. 1–4 of the subject application and is described in detail hereinbelow.

As will be discussed, the complex construction of the Cloward™ device encumbers its disassembly, and it is therefore difficult to clean and sterilize after use. It would be beneficial to provide a dowel cutter for use with a powered surgical drill that can be easily disassembled for cleaning. The subject invention describes such a device.

SUMMARY OF THE INVENTION

The subject invention is directed to a device for cutting and forming dowels from a bone mass for subsequent use as prostheses during osteopathic surgical procedures. The device is configured for use with a powered drill which includes an elongated barrel section having a chuck provided at a distal end thereof. In a preferred embodiment of the subject invention, the dowel cutting assembly includes an axial mounting member having a proximal end portion configured for engagement with the chuck, and a distal end portion configured to receive a cylindrical cutting blade. An elongated supporting shaft having a distal end portion configured to support a drill guide pin is mounted for coaxial movement with respect to the axial mounting member, and means are provided which are integral with the mounting member for releasably maintaining the relative orientation of the supporting shaft and the axial mounting member.

In one embodiment of the subject invention, a dowel cutting assembly is provided which is particularly adapted for use with a cannulated drill that has an elongated axial bore extending through the barrel section thereof. In such an embodiment, the elongated supporting shaft of the dowel cutting assembly is configured to extend through the axial bore of the drill and has a plunger provided at the proximal end thereof for facilitating axial movement of the supporting shaft. In another embodiment of the subject invention, the supporting shaft is spring biased in a distal direction and threaded means are integrally associated with the mounting member for engaging the supporting shaft to releasably maintain the relative orientation thereof with respect to the axial mounting member. In yet another embodiment of the subject invention, the elongated supporting shaft has a transverse flange formed at a proximal end thereof and a transverse slot is formed in a distal portion of the mounting member for releasably engaging the flange to maintain the relative orientation of the supporting shaft and the axial mounting member.

These and other features of the bone dowel cutter of the subject invention will become more readily apparent from the following detailed description of the invention taken in conjunction with the drawings.

BRIEF DESCRIPTION OF THE DRAWINGS

So that one skilled in the art to which the subject invention appertains will better understand how to make and use the bone dowel cutter of the subject invention, preferred embodiments thereof, as well as an embodiment of a prior art device, will be described hereinbelow with reference to the drawings wherein:

FIG. 2 is a side elevational view of the prior art dowel cutting assembly illustrated in FIG. 1 with the drill guide shaft locked in a distal position and the drill guide penetrating into a bone mass;

FIG. 3 is a side elevational view of the prior art dowel cutting assembly illustrated in FIG. 1 with the drill guide shaft in a free-movement position and the cylindrical cutting blade penetrating into the bone mass;

FIG. 4 is a side elevational view of the prior art dowel cutting assembly illustrated in FIG. 1 after the cutting blade has formed a dowel from the bone mass and the drill guide shaft has moved to a proximal position;

FIG. 5 is a side elevational view in partial cross-section of a first embodiment of a dowel cutting assembly constructed in accordance with the subject invention and adapted for utilization with a conventional cannulated powered surgical drill;

FIG. 6 is a side elevational view, with parts separated for ease of illustration, of a second embodiment of a dowel cutting assembly constructed in accordance with the subject invention and adapted for utilization with a conventional powered surgical drill;

FIG. 7 is a side elevational view of a third embodiment of a dowel cutting assembly constructed in accordance with the subject invention and adapted for utilization with a conventional surgical drill;

FIG. 8 is a perspective view of the dowel cutting assembly illustrated in FIG. 5 shown in conjunction with a conventional cannulated powered surgical drill, a conventional cylindrical cutting blade, and a conventional drill guide;

FIG. 9 is a side elevational view in partial cross-section of the dowel cutting assembly illustrated in FIG. 5 with the drill guide shaft locked in a distal position and the drill guide penetrating into a bone mass;

FIG. 10 is a side elevational view in partial cross-section of the dowel cutting assembly illustrated in FIG. 5 with the drill guide shaft in a free-movement position and the cylindrical cutting blade penetrating into the bone mass;

FIG. 11 is a side elevational view in partial cross-section of the dowel cutting assembly illustrated in FIG. 5 after the cutting blade has formed a dowel from the bone mass and the drill guide shaft has moved to a proximal position;

FIG. 12 is a side elevational view in partial cross-section of the dowel cutting assembly illustrated in FIG. 5 upon removal of the formed bone dowel from the bone mass;

FIG. 15 is a side elevational view in partial cross-section of the dowel cutting assembly illustrated in FIG. 6 with the drill guide shaft in a locked position and the drill guide penetrating into a bone mass;

FIG. 16 is a side elevational view in partial cross-section of the dowel cutting assembly illustrated in FIG. 6 with the drill guide shaft and the cylindrical cutting blade penetrating into the bone mass;

FIG. 17 is a side elevational view in partial cross-section of the prior dowel cutting assembly illustrated in FIG. 6 as the drill guide shaft is removed from the cutting assembly prior to formation of the dowel from the bone mass;

FIG. 18 is a side elevation view in partial cross-section of the dowel cutting assembly illustrated in FIG. 6 after the cylindrical cutting blade has formed the bone dowel from the bone mass;

FIG. 19 is a perspective view of the dowel cutting assembly illustrated in FIG. 7, with parts separated for ease of illustration, in conjunction with a conventional powered surgical drill, a conventional cylindrical cutting blade, and a conventional drill guide;

FIG. 20 is a side elevational view in partial cross-section of the dowel cutting assembly illustrated in FIG. 7 with the spring biased drill guide shaft locked in a distal position and the drill guide penetrating into a bone mass;

FIG. 21 is a side elevational view in partial cross-section of the dowel cutting assembly illustrated in FIG. 7 with the spring biased drill guide shaft in a free-movement position and the cylindrical cutting blade penetrating into the bone mass;

FIG. 22 is a side elevational view in partial cross-section of the dowel cutting assembly illustrated in FIG. 7 after the cutting blade has formed a dowel from the bone mass and the spring biased drill guide shaft has retracted and moved to a proximal position; and FIG. 23 is a side elevational view in partial cross-section of the dowel cutting assembly illustrated in FIG. 7 upon removal of the formed bone dowel from the bone mass with the spring biased drill guide shaft disposed in a distal position.

DETAILED DESCRIPTION OF THE PREFERRED EMBODIMENTS

Figure 1:
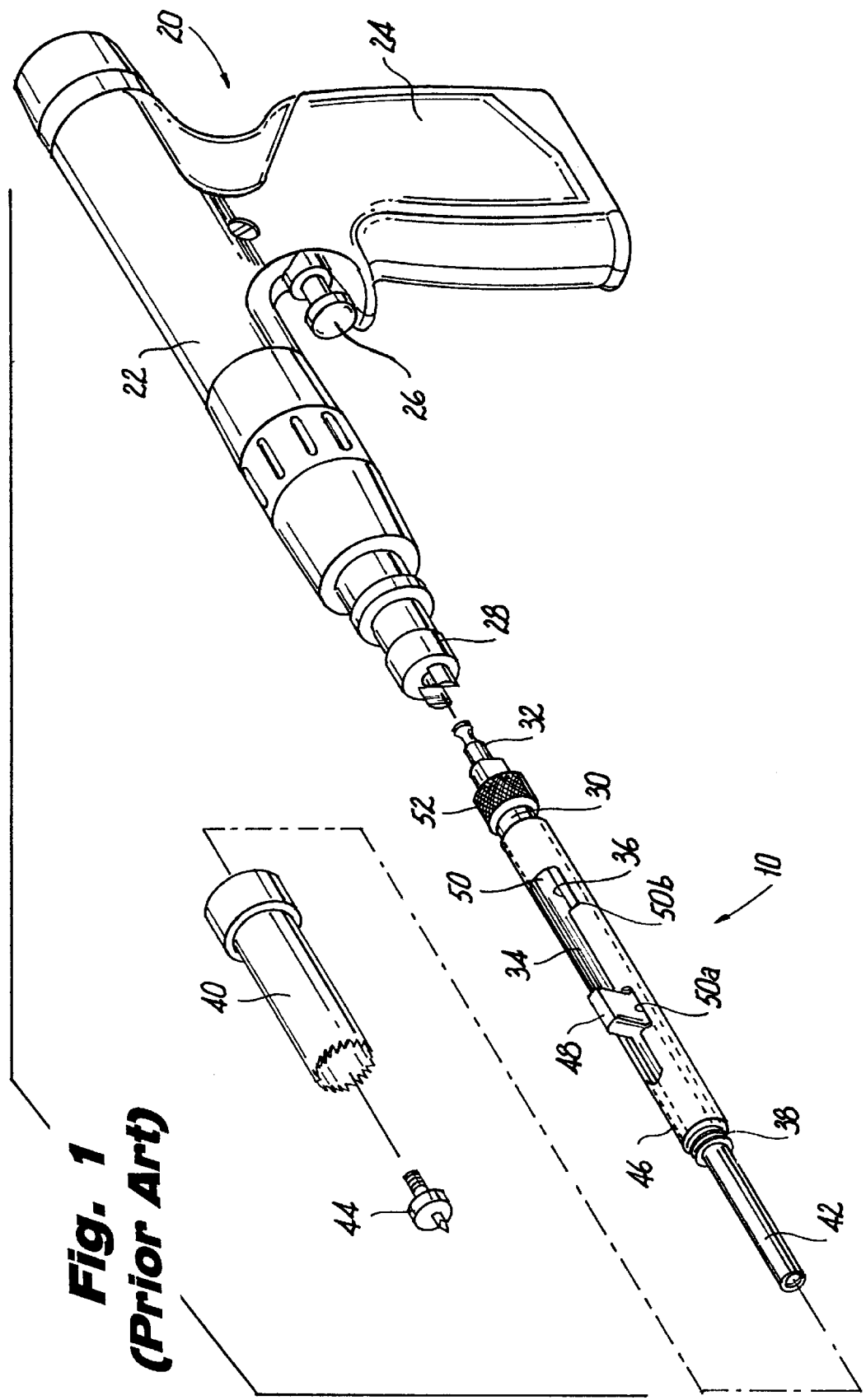
FIG. 1 is a perspective view of a prior art dowel cutting assembly shown in conjunction with a conventional powered surgical drill, a conventional cylindrical cutting blade, and a conventional drill guide.
Figure 13:
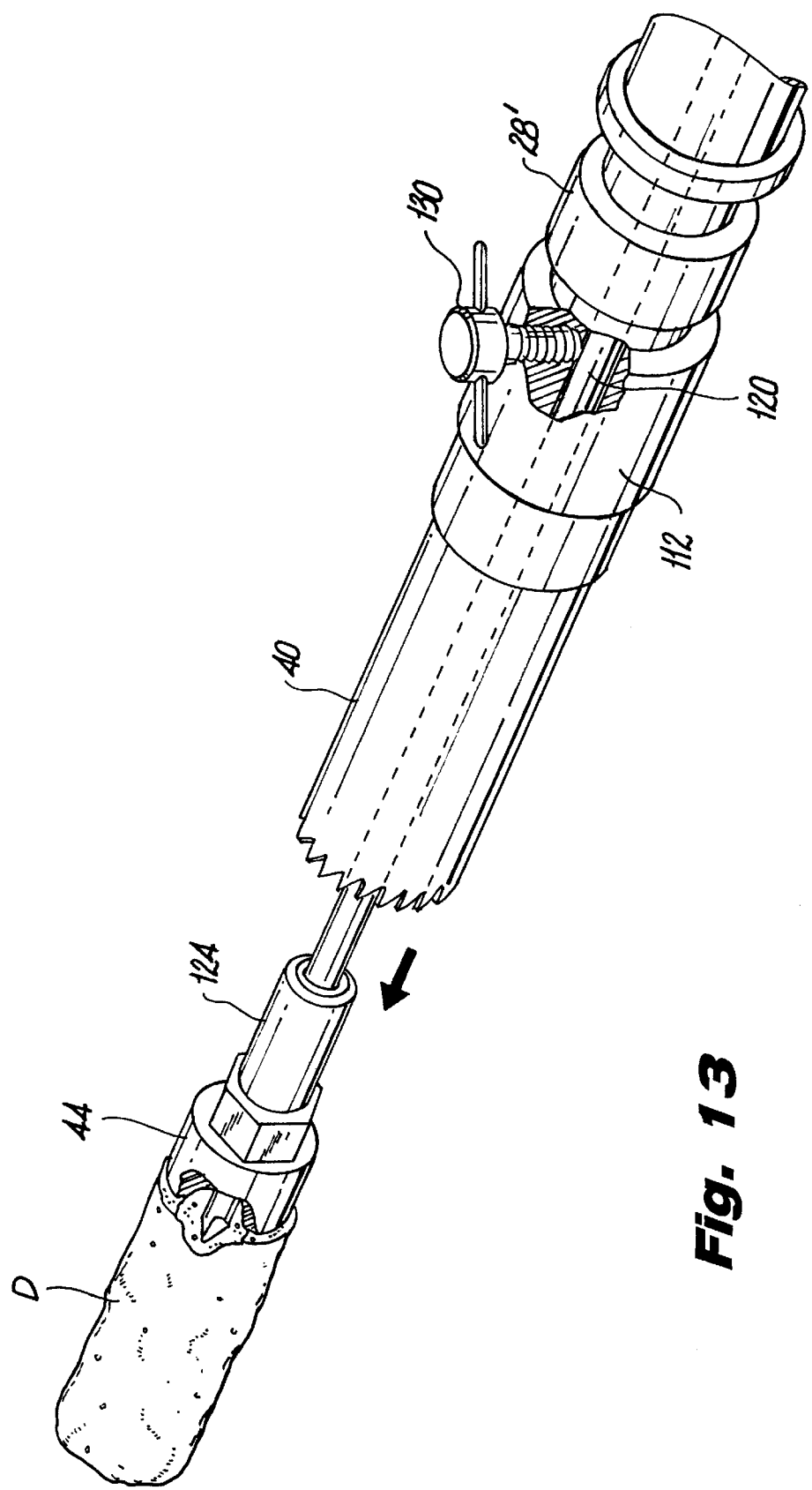
FIG. 13 is a perspective view of the dowel cutting assembly illustrated in FIG. 5 with the drill guide shaft advanced distally to expel the formed bone dowel from the cylindrical cutting blade.

In the drawings and in the description which follows, the term "proximal" as is traditional, will refer to the end of the dowel cutting assembly which is closest to the user, while the term "distal" will refer to the end of the assembly which is furthest from the user.

Referring now to the drawings, there is illustrated in FIG. 1, a prior art dowel cutting device which is designated generally by reference numeral 10. Dowel cutter 10 is distributed by Codman and Shurtleff, Inc., Randolph, Mass. 02368 (as well as others), under the Cloward™, and is adapted for use with a conventional surgical drill identified by reference numeral 20. Surgical drill 20 has an elongated barrel portion 22 and a depending handle portion 24 with a trigger 26 for actuating the drill. A chuck assembly 28 is provided at the distal end of barrel portion 22 for receiving and coupling with the proximal end of dowel cutter 10.

The prior art dowel cutter 10 includes an inner mounting shaft 30 having a proximally extending connector 32 configured for reception in chuck assembly 28 and further defining an elongated shaft body 34 having an interior bore 36 opening through the periphery and the distal end of the shaft body. A threaded area 38 is defined at the distal end of shaft body 34 for receiving a conventional cylindrical cutting blade which is identified by reference numeral 40. Dowel cutter 10 further includes an internal support shaft 42 slidably supported within interior bore 36 and having a distal end configured to threadably receive a conventional drill guide member 44. An outer sleeve 46 encloses the shaft body 34 and is axially movable with respect thereto. A slide-bolt arrangement is provided for maintaining the relative orientation of the internal support shaft 42, shaft body 34, and the outer sleeve 46 during utilization. It includes a flange 48 which extends radially outwardly from a proximal end of support shaft 42 and a coved slot 50 having distal and proximal retention areas 50a and 50b for receiving flange 48.

Turning to FIGS. 2–4, the prior art Cloward™ device is shown during a dowel forming procedure. As illustrated in FIG. 2, drill guide member 44 is extended beyond the distal end of cutting blade 40 to engage bone mass "B" and provide a pilot hole for cutting blade 40. Drill guide member 44 is maintained in this extended position through the engagement of flange 48 in distal retention area 50a. At such a time, a knurled fitting 52, which is threadably positioned on shaft body 34 adjacent the proximal end thereof, is advanced distally to impinge upon the proximal end of outer sleeve 46 and urge it distally against the proximal end of cutting blade 40, thereby further securing the position of flange 48 in retention area 50a.

After the pilot hole has been formed by drill guide member 44, flange 48 is manually released from retention area 50a, and support shaft 42 is permitted to retract proximally, as shown in FIG. 3, to enable the distal edge of cutting blade 40 to engage bone mass "B". Finally, as illustrated in FIG. 4, when cutting blade 40 is fully extended into bone mass "B", support shaft 42 is fully retracted such that flange 48 is adjacent proximal retention area 50b. At such a time, the flange may be engaged within the proximal retention area and the cutting blade may be withdrawn from the bone mass. After use, because of the complex coaxial construction of the Cloward™ device, disassembly to facilitate efficacious cleaning and sterilization is encumbered by the complexity of the device.

Referring now to FIGS. 5–7, there is illustrated three dowel cutting assemblies constructed in accordance with a preferred embodiment of the subject invention. The first dowel cutting assembly is illustrated in FIG. 5 and is designated generally by reference numeral 100. As will be discussed in detail hereinbelow, dowel cutter 100 is particularly adapted for use with a cannulated surgical drill of the type illustrated in FIG. 8. The second and third dowel cutting assemblies, which are illustrated in FIGS. 6 and 7 and designated generally by reference numerals 200 and 300, respectively, are adapted for use with a non-cannulated surgical drill, such as surgical drill 10 described earlier with respect to the prior art Cloward™ device. As will be discussed in detail hereinbelow, each of the three dowel cutters of the subject invention are easily disassembled after use, and therefore, they may be cleaned and sterilized more efficaciously than the prior art Cloward™ device.

Referring now to FIG. 8, dowel cutter 100 is illustrated in conjunction with a cannulated surgical drill 20' having an axial bore 22a extending through the barrel portion 22' thereof, a conventional cylindrical cutting blade 40, and a conventional drill guide member 44. Dowel cutter 100 includes an axial mounting member 110 having a medial body portion 112 from which extends a proximal coupling 114 and a distal threaded stem 116. The proximal coupling 114 is configured for reception within the chuck assembly 28' of cannulated drill 20', and the threaded stem 116 is configured to receive cutting blade 40.

Dowel cutter 100 further includes an elongated support shaft 120 configured to extend through axial bore 22a of the barrel portion 22' of cannulated drill 20'. A plunger 122 is provided at the proximal end of support shaft 120 for facilitating user manipulation of the shaft, and the distal end of support shaft 120 is threaded to mount a fixture 124 adapted to threadably receive drill guide member 44. A threaded fitting 130 is operatively associated with the medial body portion 112 of axial mounting member 110. Fitting 130 extends transversely through body portion 112 into the axial pathway 125 (FIG. 9) that extends longitudinally therethrough, to interact with support shaft 120 and selectively maintain the longitudinal and axial orientation thereof with respect to axial mounting member 110.

Turning now to FIGS. 9–13, there is illustrated, in sequential order, the method of utilizing dowel cutter 100 to cut and form a dowel "D" from a bone mass "B". Initially, as illustrated in FIG. 9, with threaded fitting 130 engaged against support shaft 120, drill guide member 44 is driven into bone mass "B" to form a pilot hole and properly guide the distal cutting edge of blade 40 into the bone mass. As shown in FIG. 10, once the honed cutting edge of blade 40 has penetrated the bone mass, fitting 130 is released, liberating support shaft 120, and permitting it to slidably retract proximally as the dowel is formed. Support shaft 120 continues to translate proximally until the dowel "D" is fully formed, as illustrated in FIG. 11. Thereafter, cutting blade 40 is withdrawn from bone mass "B" with the formed dowel "D" disposed therein. To remove dowel "D" from cutting blade 40, support shaft 120 is advanced distally, ejecting the formed dowel from the cutting blade.

Following the dowel cutting procedure, cutting blade 40 is removed from mounting member 110 and guide member 44 is removed from fixture 124. Then, the fixture itself is removed from the distal end of support shaft 120 and the support shaft is removed from the axial bore 22a defined in the barrel portion 22' of surgical drill 20'. Subsequently, the proximal coupling 114 is released from drill chuck 28', and thereupon dowel cutting assembly 100 is completely disassembled for cleaning and sterilization.

Figure 14:
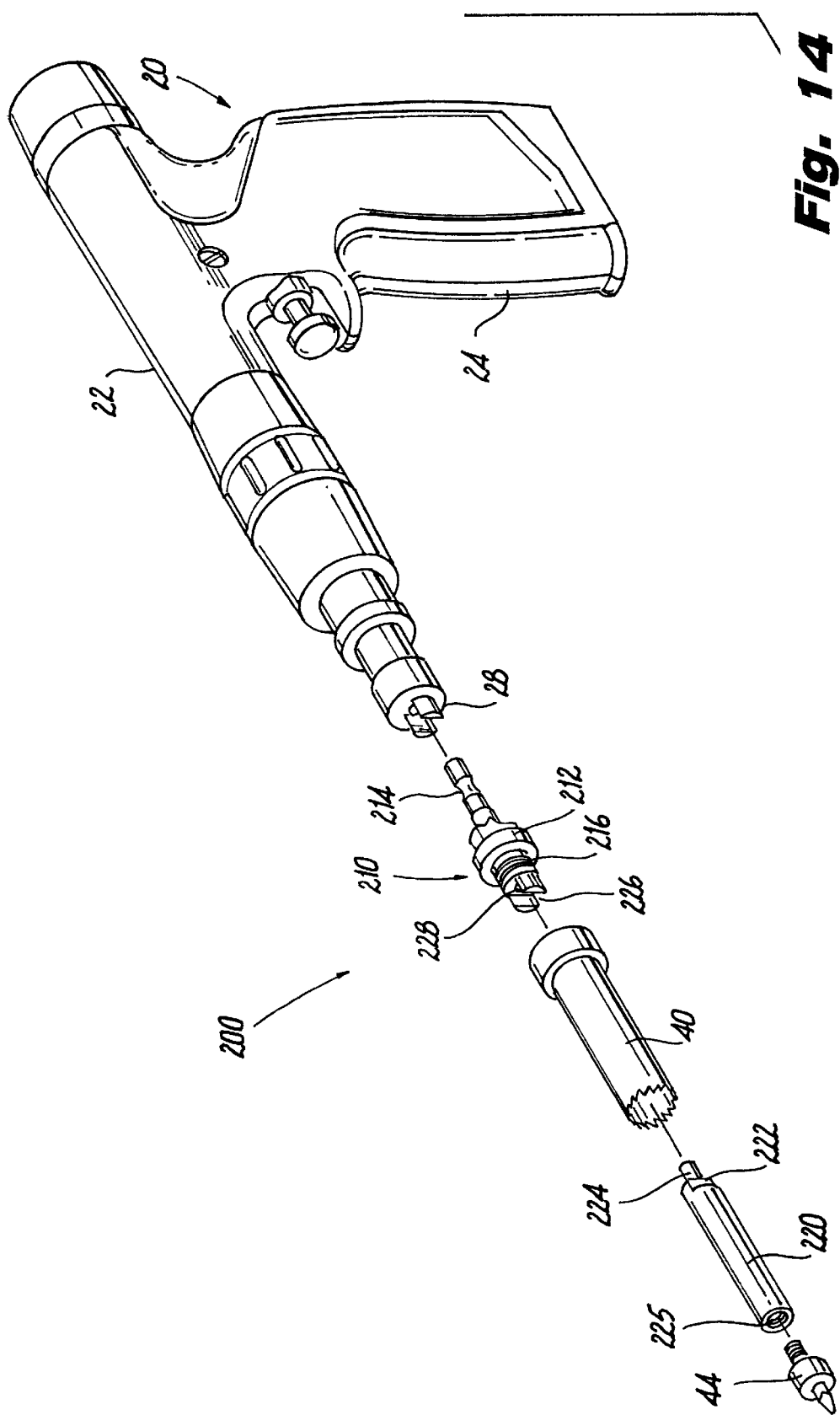
FIG. 14 is a perspective view of the dowel cutting assembly illustrated in FIG. 6 shown in conjunction with a conventional powered surgical drill, a conventional cylindrical cutting blade, and a conventional drill guide.

Referring to FIG. 14, dowel cutter 200 is illustrated in conjunction with a conventional surgical drill 20 having a barrel portion 22 with a chuck assembly 28 provided at the distal end thereof, a cutting blade 40, and a drill guide 44. Dowel cutter 200 includes an axial mounting member 210 having a medial body portion 212 from which extends proximal coupling 214 configured for reception in chuck assembly 28, and a distal threaded stem 216 configured to receive cutting blade 40.

Dowel cutter 200 further includes an elongate support shaft 220 having a threaded bore 225 extending partially therethrough from a distal end thereof to receive and mount drill guide 44. The proximal end of support shaft 220 is formed with a transverse flange 222 from which extends a cylindrical stem 224. Flange 222 and stem 224 are dimensioned and configured to engage complementary transverse slot 226 and axial bore 228 defined in mounting member 210. The engagement of these complementary structures maintains the relative axial orientation of support shaft 220 and mounting member 210 during utilization.

Referring now to FIGS. 15–18, there is illustrated, in sequential order, the method by which dowel cutter 200 is utilized to form and cut a dowel from a bone mass "B". Initially, with flange 222 and slot 226 engaged to maintain the relative axial orientation of support shaft 220 and mounting member 210, drill guide 44 is driven into bone mass "B", to guide the distal edge of cutting blade 40 toward the bone mass, as illustrated in FIG. 15. As shown in FIG. 16, the complementary structures remain engaged until the distal edge of cutting blade 40 has penetrated the bone mass. Then, as illustrated in FIG. 17, dowel cutter 200 is withdrawn from the bone mass, and support shaft 220 is disengaged from mounting member 210 and displaced from the assembly. At such a time, the cutting blade is directed back to the bone mass, and the dowel "D" is formed thereby, as shown in FIG. 18. At the conclusion of the dowel forming procedure, cutting blade 40 is removed from the distal threaded stem 216 of mounting member 210 and the proximal coupling 214 is released from drill chuck 28. Finally, drill guide 44 is detached from the distal end of support shaft 220 and the disassembled dowel cutter can be efficaciously cleaned and sterilized for subsequent utilization.

Referring to FIG. 19, dowel cutter 300 is illustrated in conjunction with drill 20, cutting blade 40, and drill guide member 44. Dowel cutter 300 includes an axial mounting member 310 having an elongate body portion 312 from which extends a proximal coupling 314 and a distal threaded stem 316. Coupling 314 is configured for reception in drill chuck 28 and stem 316 is configured to receive cutting blade 40. In addition, a stepped axial bore 315 extends through mounting member 310, decreasing in diameter within the proximal coupling 314, to accommodate support shaft assembly 320.

In this third configuration of the subject invention, support shaft 320 is spring biased in a distal direction to facilitate automatic ejection of a formed dowel from cutting blade 40 at the conclusion of a dowel forming procedure. Support shaft assembly 320 has a piston-like construction including an elongate inner rod member 322 and a coaxial outer plunger sleeve 324. A guide pin 326 extends radially outward from rod member 322 and is engaged within an elongate slot 328 formed in plunger sleeve 324 (see FIG. 22). Pin 326 and slot 328 limit the relative movement of plunger sleeve 324 with respect to rod member 322. Support shaft assembly 320 further includes a coiled compression spring 330 which is retained at its proximal end to plunger sleeve 324. A compression fitting 332 is threadably mounted to the distal end of rod member 322 and has a proximal stem 334 for retaining the distal end of compression spring 330. Fitting 332 also has a threaded bore 336 for receiving drill guide member 44. When dowel cutter 300 is assembled with support shaft assembly 320 disposed within axial mounting member 310, the proximal end of plunger sleeve 324 abuts against an internal wall 325 of stepped axial bore 315 (see FIG. 20).

Dowel cutter 300 further includes a threaded fitting 340 which is operatively associated with the elongate body portion 312 of axial mounting member 310. Fitting 340 extends transversely through body portion 312 into the distal section of axial bore 315 to interact with a proximal portion of rod member 322 and selectively maintain the longitudinal and axial orientation thereof with respect to axial mounting member 310.

Turning now to FIGS. 20–23, there is illustrated, in sequential order, a method of forming a bone dowel utilizing dowel cutter 300. First, as illustrated in FIG. 20, fitting 340 is tightened to engage rod member 322 and maintain drill guide member 44 in a distal position, extending from cutting blade 40. In this position, coiled spring 330 is in a relaxed, decompressed state. Then, as shown in FIG. 21, after drill guide 44 has penetrated into bone mass "B" and guided the honed edge of cutting blade 40 into the bone mass, threaded fitting 340 is released, thereby liberating rod member 322 to permit proximal retraction of guide member 44 against the bias of coiled spring 330.

When dowel "D" has been fully formed, and rod member 322 is in its proximal-most position, coiled spring 330 will be fully compressed. Then, as shown in FIG. 22, fitting 340 is once again tightened to engage rod member 322, and maintain the longitudinal orientation thereof with respect to mounting member 310. Once cutting blade 40 has been withdrawn from bone mass "B", fitting 340 is released, and compression spring 300 urges rod member 322 distally, ejecting the formed dowel "D" from cutting blade 40.

Following the dowel forming procedure, dowel cutter 300 is easily disassembled by removing support shaft 320 from axial mounting member 320. The compression fitting 332 is then removed from the distal end of rod member 322, and the proximal end of spring 330 is released from plunger sleeve 324. At such a time, each part of dowel cutter 300 can be effectively cleaned and sterilized for subsequent utilization.

Although the subject invention has been described with respect to preferred embodiments, it will be readily apparent to those having ordinary skill in the art to which it appertains that changes and modifications may be made thereto without departing from the spirit or scope of the subject invention as defined by the appended claims.

What is claimed is:

1. A dowel cutting assembly for use with a powered drill which includes a barrel section having a chuck provided at a distal end thereof, comprising:
   a) a mounting member having a proximal end portion configured for engagement with the chuck and a distal end portion configured for operative engagement with a cylindrical cutting blade;
   b) an elongated supporting shaft having a distal end portion configured to support a drill guide; and
   c) means for maintaining the relative longitudinal orientation of the elongated supporting shaft and the mounting member;
   wherein the mounting member includes a transverse bore and the maintaining means includes an engagement member which is movable through the transverse bore into engagement with the supporting shaft.

2. A dowel cutting assembly according to claim 1, wherein an axial bore extends at least partially through the mounting member to accommodate the proximal end of the elongated supporting shaft.

3. A dowel cutting assembly for use with a powered drill which includes a barrel section having a chuck provided at a distal end thereof, comprising:
   a) a mounting member having a proximal end portion configured for engagement with the chuck and a distal end portion configured for operative engagement with a cylindrical cutting blade;
   b) an elongated supporting shaft having a distal end portion configured to support a drill guide; and
   c) means for maintaining the relative longitudinal orientation of the elongated supporting shaft and the mounting member;
   wherein an axial bore extends at least partially through the mounting member to accommodate the proximal end of the elongated supporting shaft, the maintaining means including an engagement member operably connected to the mounting member, the engagement member being movable into engagement with the supporting shaft to maintain the relative axial orientation of the supporting shaft and axial mounting member, and wherein the mounting member includes a transverse bore and the engagement member is movable through the transverse bore into engagement with the supporting shaft.

4. A dowel cutting assembly according to claim 3, wherein the engagement member is threadably received within the transverse bore.

5. A dowel cutting assembly for use with a powered drill which includes a barrel section having a chuck provided at a distal end thereof, comprising:
   a) a mounting member having a proximal end portion configured for engagement with the chuck and a distal end portion configured for operative engagement with a cylindrical cutting blade;
   b) an elongated supporting shaft having a distal end portion configured to support a drill guide; and
   c) means for maintaining the relative longitudinal orientation of the elongated supporting shaft and the mounting member,
   wherein an axial bore extends at least partially through the mounting member to accommodate the proximal end of the elongated supporting shaft, the elongated supporting shaft including an elongate support rod, a sleeve movably supported about the support rod, and a compression spring mounted about the sleeve.

6. A dowel cutting assembly according to claim 5, wherein a drill guide is operatively connected to the distal end of the elongate support rod.

7. A dowel cutting assembly according to claim 6, wherein the proximal end of the support rod is positioned and configured to be slidable within the axial bore formed in the mounting member.

8. A dowel cutting assembly according to claim 7, wherein the proximal end of the compression spring is fastened to the sleeve and the distal end of the compression spring abuts against a fitting fastened to the distal end of the elongate support rod, the compression spring urging the mounting member proximally and the drill guide distally.

9. A dowel cutting assembly according to claim 8, further comprising a cylindrical cutting blade supported on the mounting member, the cutting blade being positioned about the elongated supporting shaft.

10. A dowel cutting assembly according to claim 1, further comprising a cylindrical cutting blade operatively connected to the mounting member, the cylindrical cutting blade being positioned about the elongated supporting shaft.

11. A dowel cutting assembly according to claim 10, further comprising a drill guide operatively connected to the distal end of the elongated shaft, the drill guide extending distally beyond the distal edge of the cylindrical cutting blade.

12. A dowel cutting assembly for use with a powered drill which includes a barrel section having a chuck provided at a distal end thereof, comprising:
   a) a mounting member having a proximal end portion configured for engagement with the chuck and a distal end portion configured for operative engagement with a cylindrical cutting blade;
   b) an elongated supporting shaft having a distal end portion configured to support a drill guide;
   c) means for maintaining the relative longitudinal orientation of the elongated supporting shaft and the mounting member;
   d) a cylindrical cutting blade operatively connected to the mounting member the cylindrical cutting blade being positioned about the elongated supporting shaft; and
   e) a drill guide operatively connected to the distal end of the elongated shaft, the drill guide extending distally beyond the distal edge of the cylindrical cutting blade;
   wherein the maintaining means includes an abutment surface formed on the mounting member.

13. A dowel cutting assembly according to claim 12, wherein the elongated supporting shaft has a transverse flange formed at a proximal end thereof and the abutment surface has a transverse slot configured to receive the transverse flange.

14. A dowel cutting assembly according to claim 10, wherein a threaded stem extends distally from the mounting member for threadably engaging the cylindrical cutting blade.

* * * * *